(12) United States Patent
McFarland et al.

(10) Patent No.: US 10,929,510 B2
(45) Date of Patent: Feb. 23, 2021

(54) PATIENT CARE SYSTEMS EMPLOYING CONTROL DEVICES TO IDENTIFY AND CONFIGURE SENSOR DEVICES FOR PATIENTS

(71) Applicant: Preventice Technologies, Inc., Rochester, MN (US)

(72) Inventors: Gale G. McFarland, Rochester, MN (US); Kevin W. Kirkeby, Rochester, MN (US); James D. Hutchins, Kernersville, NC (US); Richard M. Smith, Oronoco, MN (US)

(73) Assignee: Preventice Technologies, Inc., Rochester, MN (US)

( * ) Notice: Subject to any disclaimer, the term of this patent is extended or adjusted under 35 U.S.C. 154(b) by 1366 days.

(21) Appl. No.: 14/973,511

(22) Filed: Dec. 17, 2015

(65) Prior Publication Data

US 2017/0177811 A1    Jun. 22, 2017

(51) Int. Cl.
  *G06F 19/00*   (2018.01)
  *G16H 40/40*   (2018.01)
  *G16H 50/20*   (2018.01)
  *G16H 10/60*   (2018.01)

(52) U.S. Cl.
  CPC ......... *G06F 19/3456* (2013.01); *G16H 10/60* (2018.01); *G16H 40/40* (2018.01); *G16H 50/20* (2018.01)

(58) Field of Classification Search
  CPC ........ G16H 10/60; G16H 40/40; G16H 50/20; G06F 19/3456

USPC ......................................................... 705/2–3
See application file for complete search history.

(56) References Cited

U.S. PATENT DOCUMENTS

| 2006/0161054 | A1* | 7/2006 | Reuss | A61B 5/14542 600/300 |
| 2011/0021140 | A1* | 1/2011 | Binier | G06F 19/328 455/41.1 |
| 2015/0363563 | A1* | 12/2015 | Hallwachs | G16H 80/00 705/3 |

OTHER PUBLICATIONS

GSM Association, Connected Mobile Health Devices: A Reference Architecture, Jan. 2011, GSM Association, Version 1.0, pp. 1-39 (Year: 2011).*
PCT/US2016/061481, International Search Report, dated Jan. 25, 2017, 11 pages.

* cited by examiner

*Primary Examiner* — Joy Chng
(74) *Attorney, Agent, or Firm* — Patterson + Sheridan, LLP

(57) ABSTRACT

Embodiments provide techniques for authenticating and configuring a care plan device in a care plan environment. Embodiments receive, from the care plan device, a care plan device identifier written to a memory of the care plan device by a manufacturer. The care plan device is authenticated with a remote server, based on matching a reference identifier within a patient care plan with the care plan device identifier. Upon authenticating the care plan device, embodiments receive, from the remote server, the configuration information for the care plan device. The care plan device is configured in accordance with the patient care plan, based on the received configuration information.

20 Claims, 7 Drawing Sheets

PATIENT CARE SYSTEMS EMPLOYING CONTROL DEVICES TO IDENTIFY AND CONFIGURE SENSOR DEVICES FOR PATIENTS

BACKGROUND

Field

The present disclosure relates to decision-support systems for patient healthcare, and in particular, to identify and configure medical devices.

Description of the Related Art

Through advances in information technology, modern healthcare providers can quickly and easily visualize health conditions and vital statistics for a patient. For instance, biometric sensors may detect at least one health condition including a vital statistic of a patient and generate a signal including data based on the condition. For example, biometric sensors could be used to detect health conditions in the form of heart rate data, electrocardiogram data, blood pressure data, blood sugar data, weight, and so on for a patient. These observations may be collected over time and presented to health care providers caring for the patient. For example, a health care provider could monitor health observations for the patient over extended timeframes, e.g., twenty-four hours or more, to monitor the health of the patient and to identify possible abnormalities. The abnormalities may be observable as changes in the biometric data. The abnormalities may be used by the medical care provider to provide long term care to the patient, predict future medical events, or to diagnose medical conditions of the patient.

In order to facilitate the detection and use of biometric data, medical diagnostic equipment needs to be efficiently delivered to the patient and configured for data communication so that use may begin. Many challenges have prevented a more widespread use of affordable medical equipment employing information technology to capture and transmit biometric data. One challenge is related to supply chain issues when physically providing the specific types of equipment to patients. If the wrong equipment is provided then unwanted gaps in patient care may occur as new and more appropriate equipment is transported to the patient so that the patient may begin their prescribed prescription period in a timely manner. Setup of delivered equipment is also challenging. Patients may be mentally or physically impaired due to medical conditions (e.g., 80 year old recent heart attack patient with large hands) and these impaired patients may have difficulty following setup procedures to enable their equipment to begin operation. Further, medical or technical staffs available to assist such patients may be in short supply and increase the cost of maintaining this equipment. Accordingly, new approaches are needed to enable more efficient delivery and setup of medical equipment to patients.

SUMMARY

Disclosed herein are patient care systems employing control devices to identify and configure sensor devices for patients. A care plan created by a care provider of a patient specifies to measure a health condition of the patient using a monitoring device. A remote server may include the care plan defined by the provider, configuration information for the at least one monitoring device, and patient-specific information. The provider may also physically send the at least one monitoring device to the patient as part of a kit. By providing the patient with a control device, at least a portion of the kit may be identified and configured for use consistent with the plan. The control device may also facilitate patient-specific and health condition information to be exchanged between the monitoring device and the remote server. In this manner, the health condition may be monitored according to the plan.

One embodiment provides a method that includes authenticating, with the remote server, a control device based on matching a reference identifier received from a storage device with a control device identifier received from the control device. The storage device includes association relationships between: a reference identifier, patient-specific information, and configuration information for a monitoring device. Upon authenticating the control device, the method includes sending, from the remote server to the control device, the configuration information for the monitoring device linked by the association relationships to the reference identifier. The method also includes establishing a connection, with the control device, between the control device and the monitoring device based on the configuration information.

Other embodiments include a control device that includes logic configured to carry out the aforementioned method and a computer-readable medium containing computer program code that, when executed, carries out the aforementioned method.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, which may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

At least one sensor device as specified in a care plan for a patient provides opportunities for a care provider (e.g., a physician, nurse, technician, etc.) to improve patient care. A workflow server can utilize data provided by the at least one sensor device or an "internet of things" (IoT) device to identify health events that range from identifying critical health care issues such as cardiac or respiratory emergencies to maintenance events where the sensor device fails, e.g., because a battery is low or a wire is disconnected. The types of data and the sensor devices utilized to provide the data may change over the course of a treatment of the patient as specified by the care plan defined by the care provider. The care plan may also be modified by the care provider as needed to meet the changing needs of the patient. To detect health related events, the at least one sensor device in one example is included as part of a kit provided by the care provider to the patient. The kit may include other sensor devices which may or may not be specified by the care plan for use by the patient. The patient is provided a control device consistent with the care plan as defined by the care provider. The control device is in communication with a remote server where the care plan is located. The remote server also includes configuration information, which upon transfer to the control device, enables connectivity of the control device to respective ones of the at least one sensor devices. The remote server also includes patient-specific information (e.g., maximum diastolic blood pressure) which may be downloaded from the remote server to the at least one sensor device and/or the control device to enable the at least one sensor to provide immediate feedback to the patient or change operation. For example, the sensor device may be a stress test apparatus (e.g., recumbent bicycle) which may change resistance to the patient during use when the health condition data of the patient exceeds some threshold as included in the patient-specific information downloaded from the remote server. The care plan may also be changed over time to enable the care provider to specify different health conditions to be measured by different sensor devices according to the patient-specific information. In this manner, the health condition of the patient may be efficiently monitored over time according to the care plan.

Figure 1:
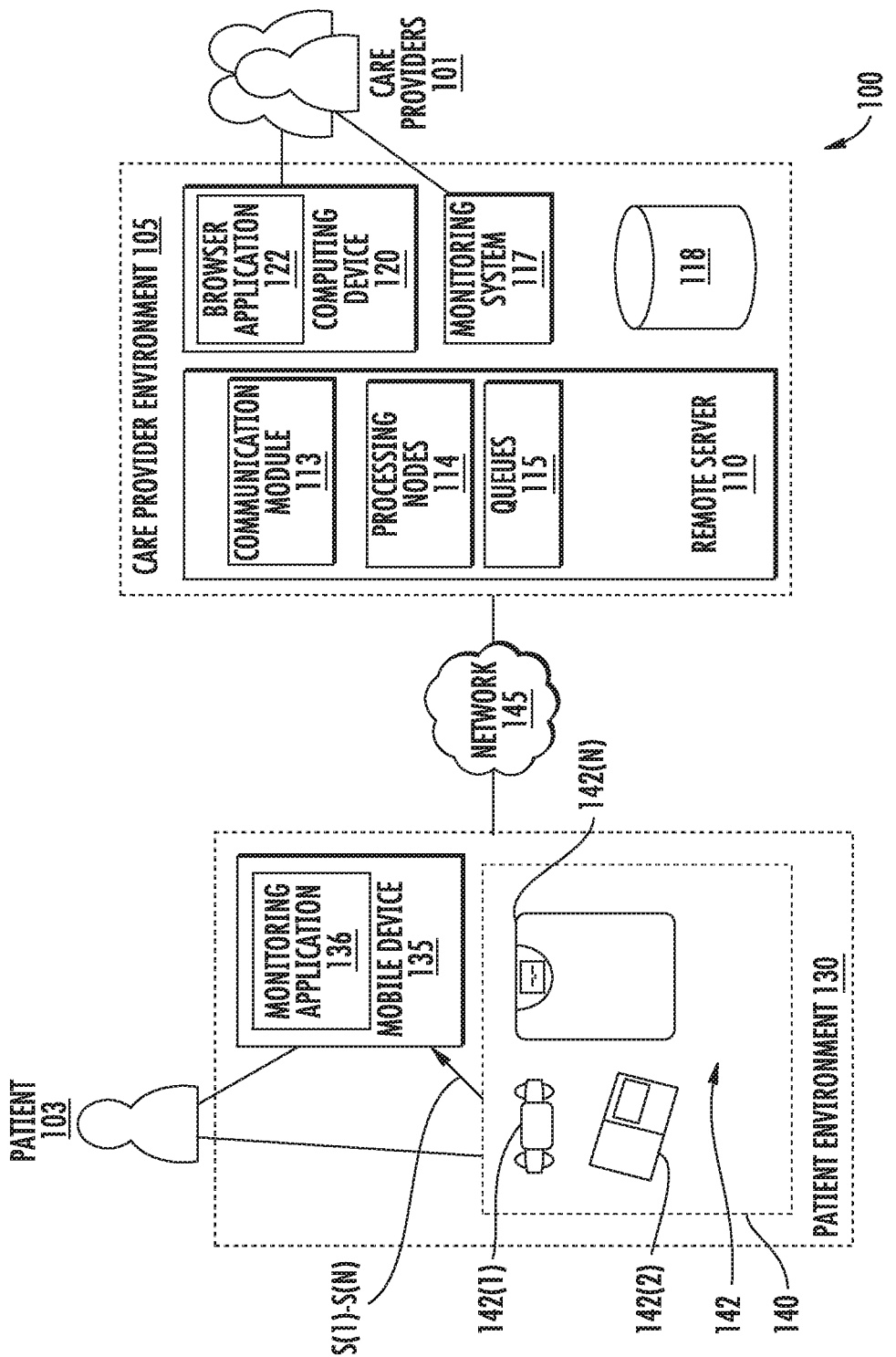
FIG. 1 is a schematic drawing of an exemplary computing and physical environment, according to one embodiment, comprising a care provider environment and a patient environment including at least one sensor device in the proximity of a patient, according to one embodiment described herein.

In this regard, FIG. 1 illustrates an example computing environment 100, according to one embodiment. As shown, the computing environment 100 may include a care provider environment 105 and a patient environment 130, each connected to one another via a network 145. The care provider environment 105 and the patient environment 130 allow one or more care providers 101 (e.g., a technician, nurse, physician, etc.) to monitor health condition data collected from the patient 103 in the patient environment 130 by at least one sensor device 142(1)-142(N).

The care provider environment 105 may include a remote server 110, a computing device 120, a monitoring system 117, and a data repository 118. In one example, the data repository 118 may be incorporated as part of the remote server 110. Each of the remote server 110, the computing device 120, and the monitoring system 117 may be a physical computing system that includes one or more computing devices or a virtual computer instance (e.g., executing in a cloud computing platform). A care provider 101 may use the computing device 120 to access (e.g., via a browser application 122, a native application on the computing devices 120, etc.) a user interface (UI) hosted by the monitoring system 117.

The remote server 110 includes applications and data executed to identify and handle health events corresponding to the patient 103. As shown, remote server 110 includes a communication module 113, processing nodes 114, and queues 115. In one embodiment, the processing nodes 114 are software code or applications that perform a predetermined task or action on received data (e.g., health events). The remote server 110 evaluates data received from the patient environment 130 using a set of interconnected processing nodes 114 and the queues 115 which form a workflow. As the health condition data (e.g., biometric data or health events) are received from the patient environment 130, the remote server may classify (or reclassify) the data to identify a type of the health event or an appropriate action to take in response—e.g., presentation or notification to patient/care provider, suppression, classification, aggregation, computation, prioritization/triage, and the like. For example, different types of data received from the patient environment 130 may trigger different types of health events—e.g., an irregular heartbeat may trigger a cardiac event, while a signal indicating a biometric sensor has become detached triggers a maintenance event. In one embodiment, the at least one sensor device 142(1)-142(N) within the patient environment 130 or a monitoring application 136 installed as part of a control device 135 within the patient environment 130 may have performed an initial classification of the data or health events. Nonetheless, the remote server 110 may evaluate the biometric data (or maintenance data) to confirm that this initial classification was correct.

The communication module 113 permits the remote server 110 to receive the data from the patient environment 130 and transmit data to the care providers 101. The communication module 113 may receive data from the at least one sensor device 142(1)-142(N) which is used to identify a health event and a corresponding path through interconnected ones of the processing nodes 114 and the queues 115. The communication module 113 helps the care providers 101 complete the workflow by use of the monitoring system 117 and the computing device 120. Moreover, in addition to receiving the data from the patient environment 130, the communication module 113 may enable the remote server 110 to transmit requests or instructions to the patient environment 130 such as asking the patient 103 if he or she has any symptoms or instructing the patient 103 to reattach the at least one sensor device 142(1)-142(N) which may have become disconnected.

With continued reference to FIG. 1, the patient environment 130 includes the control device 135 and the at least one sensor device 142(1)-142(N). The control device 135 (e.g., a mobile device) includes the monitoring application 136 which permits communication between the at least one sensor device 142(1)-142(N) and the care provider environment 105 via the network 145. The monitoring application 136 may configure the at least one sensor device 142(1)-142(N) (e.g., internet of things (IoT) devices) to monitor biometric data of the patient 103 as specified by a care plan. For example, the monitoring application 136 could configure logic on a heart rate monitoring device worn by the patient to monitor the patient's heart rate. Each of the one or more sensor devices 142(1)-142(N) may send the sensed data S(1)-S(N) to the monitoring application 136. In turn, the monitoring application 136 can send the heart rate data to the remote server 110 which determines if a health event is triggered, and if so, executes a workflow to process the event as described above. In another embodiment, the heart rate monitoring device, upon detecting that a threshold condition has been satisfied, could generate and transmit a health event to the control device 135, which in turn transmits the health event to the remote server 110 for processing. However, in other embodiments, some of the tasks performed by the remote server 110 may be performed in the patient environment. That is, the workflow may include tasks performed by the control device 135 or the at least one sensor device 142(1)-142(N) as well as tasks performed by the remote server 110.

In one embodiment, the monitoring application 136 receives environmental data from the at least one sensor device 142(1)-142(N). Generally, the environmental data informs the monitoring application 136 of environmental conditions in an area proximate to the at least one sensor device 142(1)-142(N) and the user—e.g., a room in which the user is located. For example, the at least one sensor device 142(1)-142(N) may detect an air quality or pollen count for a patient 103 having a respiratory ailment. In another example, the at least one sensor device 142(1)-142(N) may track the user's movements or actions in an environment such as how many times at night the patient 103 goes to the bathroom or if the patient 103 is tossing and turning at night. This environmental data can then be used by the monitoring application 136 by itself, or in combination with the biometric data, to trigger health events which are processed by the remote server 110.

In one embodiment, the monitoring application 136 may use an output device (e.g., a display or audio system) on the control device 135 to provide information to the patient 103. For example, when executing a workflow, one of the processing nodes 114 may ask the patient 103 if she is experiencing any symptoms. To obtain feedback from the patient 103, the monitoring application 136 may display a user interface (UI) on the control device 135 which permits the patient 103 to list symptoms. Moreover, the monitoring application 136 may also display general information related to a care plan or the sensor devices 142(1)-142(N) such as the patient's heart rate or weight, status of the sensor devices 142(1)-142(N), etc. Additionally, various sensor devices 142(1)-142(N) can be used to provide feedback to the patient. For example, a sensor device 142(1)-142(N) could be equipped with an input/output device (e.g., a display device, one or more speakers, light-emitting diodes, etc.) that can be used to provide feedback to the patient.

In one embodiment, the sensor devices 142(1)-142(N) interacts with the monitoring application 136 and assists the patient 103 in reporting patient vitals and other information to the care provider environment 105. As shown, the sensor devices 142(1)-142(N) may be part of a kit 140. The kit 140 may include a body sensor such as an electrocardiogram (ECG) sensor 142(1), a blood pressure cuff 142(2), and a weighing scale 142(N). Each of the sensor devices 140 may capture different vitals of the patient 103. For example, when applied to a body of patient 103, the body sensor 142(1) captures real-time biometric data (e.g., heart rate, ECG data, etc.). In addition, each of the sensor devices 142(1)-142(N) may be configured to transmit body-related metrics electronically to the monitoring application 136 on the control device 135. In turn, the monitoring application 136 sends the captured metrics to the remote server 110 which can be used to trigger health events which are processed using the processing nodes 114 and the queues 115.

In one embodiment, upon detecting an observation threshold has been reached, the sensor devices 142(1)-142(N) performs an initial classification of the health event. In a particular embodiment, the control device 135 is configured to perform the initial classification of the health event. For example, the ECG sensor 142(1), upon detecting that ECG data collected from the patient 103 indicates an erratic heart behavior, could classify the health event as a cardiac event. This initial classification of the health event, along with the relevant ECG data (e.g., ECG data including a predetermined length of time before and after the event), could be transmitted to the control device 135 (e.g., over a Bluetooth® communications link) and the monitoring application 136 subsequently forwards the ECG data and the health event data on to the remote server 110 over the network 145 (e.g., the Internet). Alternatively, the monitoring application 136 may perform the initial classification, and transmit the initial classification along with the relevant ECG data to the remote server. In yet another embodiment, instead of classifying the data, the monitoring application 136 may forward the raw, unprocessed sensor data to the remote server 110 which uses one or more of the processing nodes 114 to identify and classify health events which are then processed in the remote server 110.

Figure 2:
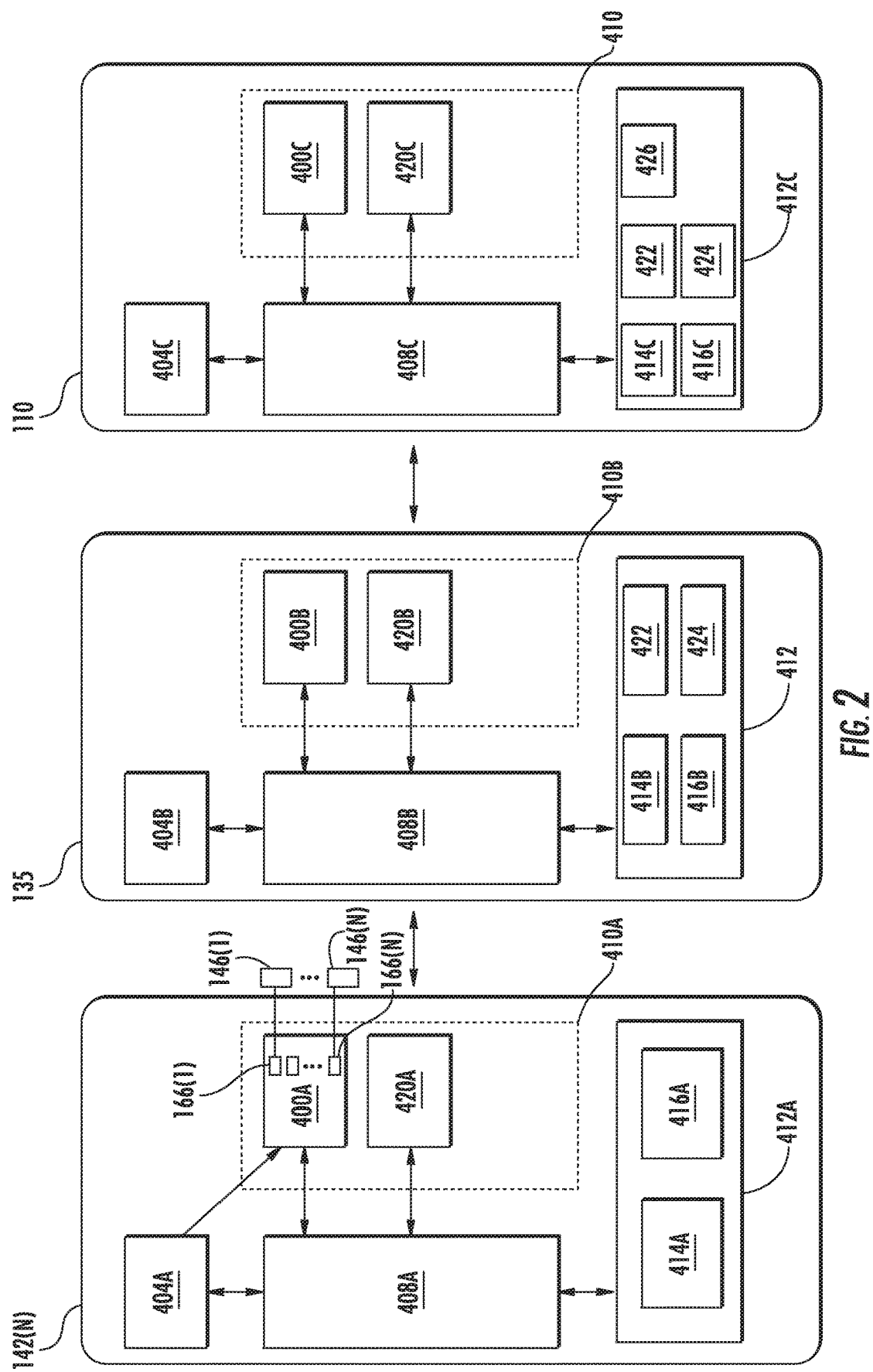
FIG. 2 is a schematic drawing of exemplary components of the at least one sensor device, the control device, and the remote server in communication with each other within the care provider environment and the patient environment of FIG. 1, according to one embodiment described herein.

FIG. 2 is a schematic diagram of exemplary components of the at least one sensor device 142(N), the control device 135, and the remote server 110 in communication with each other. In general, the sensor device 142(N), the control device 135, and the remote server 110 can each be computing devices and now will be discussed sequentially.

The sensor devices 142(1)-142(N) are each specified for use by the care plan assigned to the patient 103 by the care provider. The sensor devices 142(1)-142(N) generate health condition data S(1)-S(N) (FIG. 1) indicative of the health of the patient 103 An example of the sensor device 142(1)-142(N) may include, but is not limited to a body sensor 142(1) such as a BodyGuardian® Remote Monitoring System available from Preventice Technologies, Inc. of Rochester, Minn. or other similar device. The sensor devices 142(1)-142(N) may each include a power source 404A, a memory unit 412A, a processor 408A, and input/output (I/O) devices 410A. These electrical components are now discussed sequentially.

In this regard, the sensor device 142(N) may be battery-operated from the power source 404A, although the sensor device 142(N) may at one time or another receive power from a wired connection to a wall outlet, wireless charger or other similar devices without deviating from the basic scope of the disclosure provided herein. The power source 404A may supply power to the memory unit 412A, the processor 408A, and the I/O devices 410A. Further, the power source 404A may be able to provide voltages to at least one biometric sensor 146(1)-146(N) of the sensor device 142 of opposite polarity (or one positive voltage and one reference voltage). In other embodiments or other operational modes involving the power source 404A, the biometric sensor 146 may transmit the health condition data S(1)-S(N) to the sensor device 142 in a passive manner, wherein the passive manner involves transmitting the health condition data S(1)-S(N) to the sensor device 142 without the biometric sensor 146 consuming power from the power source 404A. Specifically, the biometric sensors 146(1)-146(N) may detect the tiny electrical changes on the skin of the patient 103 that arise from the heart muscle during each heartbeat or measure other health conditions of the patient 103. Using these approaches, the power source 404A may be used to facilitate the operation of the sensor device 142(N) as the sensor device 142(N) is coupled to the biometric sensors 146(1)-146(N) via a bridge connector 144.

With continued reference to FIG. 2, the memory unit 412A of the sensor device 142(N) contains data and instructions to facilitate the operation of the sensor device 142(N). In this regard, the memory unit 412A may be in communication with the processor 408A and include one or more software applications 414A that, when executed by the processor 408A may facilitate the operation of the sensor device 142(N). The memory unit 412A may also include storage capacity for stored health condition data 416A which may be sent to the memory unit 412A by the processor 408A and retrieved as needed by the processor 408A for analysis or transmittal to the control device 135 and/or the network 145 (FIG. 1). The stored health condition information 416A may include any type of information that relates to the health condition of the patient (i.e, electrocardiogram data over time), patient user data, electronic device configuration data, device control rules or other useful information, which are discussed further below. The stored health condition information 416A may include information that is delivered to and/or received from another of the at least one sensor devices 142(1)-142(N) (FIG. 1). The stored health condition information 416A may reflect various data files, settings and/or parameters associated with the environment, device control rules and/or desired behavior of the sensor device 142. The memory unit 412A may comprise a computer-readable medium and may comprise volatile or non-volatile memory units, for example, dynamic random access memory (DRAM) units. The memory unit 412A may be any technically feasible type of hardware unit configured to store data. For example, the memory unit 412A could be a hard disk, a random access memory (RAM) module, a flash memory unit, or a combination of different hardware units configured to store data. In this manner, the memory unit 412A contains data and instructions needed for operation of the sensor device 142(N).

The processor 408A of the sensor device 142(N) coordinates the activities of the memory unit 412A, and I/O devices 410A. The processor 408A may be a hardware unit or combination of hardware units capable of executing software applications and processing data. In some configurations, the processor 408A includes a central processing unit (CPU), a digital signal processor (DSP), an application-specific integrated circuit (ASIC), and/or a combination of such units. The processor 408A is generally configured to execute the one or more software applications 414A and process the stored health condition data 416A, which may be each included within the memory unit 412A or in other embodiments at least partially resident in the processor 408A. In this manner, the processor 408A facilitates the operation of the sensor device 142(N).

The I/O devices 410A of the sensor device 142A are coupled to the memory unit 412A and the processor 408A, and may include devices capable of receiving input and/or devices capable of providing output. The I/O devices 410A may include a signal processing device 400A and one or more wireless transceivers 420A. The signal processing device 400A includes device ports 166(1)-166(N) to communicate with the biometric sensors 146(1)-146(N) and receive the health condition data S(1)-S(N) generated by the biometric sensors 146(1)-146(N). The signal processing device 400A may amplify and/or filter the health condition data S(1)-S(N) from the biometric sensors 146(1)-146(N) before transferring the health condition data S(1)-S(N) to the processor 408A which may perform further operations, for example, further data modification, analysis, storage, or transmittal. In this manner, the sensor device 142(N) may receive the health condition data S(1)-S(N) generated by the biometric sensors 146(1)-146(N) and make the health condition data S(1)-S(N) available for further analysis, storage, or transmission.

Moreover, the I/O devices 410A of the sensor device 142(N) may include one or more wireless transceivers 420A. Each of the wireless transceivers 420A may be configured to establish one or more different types of wired or wireless communication links with other transceivers residing within other computing devices, such as the control device 135 (FIG. 1) or other devices in the network 145 (FIG. 1). A given transceiver 420A within the I/O devices 410A could establish, for example, a Wi-Fi communication link, near field communication (NFC) link or a Bluetooth® communication link (e.g., BTLE, Bluetooth classic). The I/O devices 410A of the sensor device 142(N) may have an identifier (e.g., MAC address) and a password (e.g., Bluetooth key) that are used to establish connectivity with the control device 135, so that patient-specific information may be received from the control device 135 and the health condition data S(1)-S(N) may be transferred to the control device 135. The patient-specific information may be used by the sensor device 142(N) to modify limits in the operation of the sensor device 142(N) and/or the limits of the health condition data S(1)-S(N) generated during analysis so that health events (e.g., abnormal ECG trace, abnormal blood pressure, etc.) can be detected and identified at the sensor device 142(N). The I/O devices 410A may also receive enable or disable codes so that the sensor device 142(N) will become available or unavailable for use by the patient 103 according to the care plan assigned to the patient 103 by a care provider. In this manner, the I/O devices 410A of the sensor device 142(N) may make the health condition data S(1)-S(N) of the patient 103 available to the care providers 101 and/or the care provider environment 105 according to the care plan.

With continued reference to FIG. 2, the control device 135 receives information from the remote server 110, so that the one or more sensor devices 142(1)-142(N) specified in the care plan assigned to a patient 103 are enabled for use by the patient according to the care plan. The sensor devices are provided with the patient-specific information to better interact with the patient 103. The components of the control device 135 are similar to the components of the sensor device 142(N), and so mainly differences are discussed in the interest of clarity and conciseness. The components of the control device 135 are designated with a "B" instead of an "A" to suggest this similarity.

The memory unit 412B of the control device 135 is configured to contain data and instructions to facilitate the operation of the control device 135. In this regard, the memory unit 412B may be in communication with the processor 408B and include one or more software applications 414B that, when executed by the processor 408B may facilitate the operation of the control device 135. The memory unit 412B may also include storage capacity for the stored health condition data 416B which may be sent to the memory unit 412B by the processor 408B and retrieved as needed by the processor 408B for analysis or transmittal to the remote server 110. The memory unit 412B may also include storage capacity for configuration information 422 received from the remote server 110. The configuration information 422 enables the software applications 414B of the control device 135 to establish connectivity with the sensor device 142(N) via the I/O devices 410B of the control device 135. The configuration information 422 may include the identifier information (e.g., MAC address) and the password of the sensor device 142(N). The memory unit 412B may also include storage capacity for the patient-specific information 424 received from the remote server 110. The patient-specific information 424 may be transferred to the sensor device 142(N) once connectivity is established between the control device 135 and the sensor device 142(N). In this manner, the memory unit 412B contains data and instructions needed for establishing connectivity with the sensor device 142(N) specified for use with the patient 103 according to the care plan for operation of the sensor devices 142(1)-142(N).

With continued reference to FIG. 2, the remote server 110 receives information from the computing device 120 (FIG. 1) regarding the care plan assigned each patient 103, so that the remote server 110 may identify the control device 135 and the sensor device 142(N) assigned to the patient and operate these devices consistent with the care plan. The components of the remote server 110 are similar to those of the control device 135, and so mainly differences are discussed in the interest of clarity and conciseness. The components of the remote server 110 are designated with a "C" instead of a "B" to suggest this similarity.

The memory unit 412C of the remote server 110 is configured to contain data and instructions to facilitate operation of the remote server 110. In this regard, the memory unit 412C may be in communication with the processor 408C and include one or more software applications 414C that, when executed by the processor 408C may facilitate the operation of the remote server 110. The memory unit 412C may also include storage capacity for the stored health condition data 416C which may be sent to the memory unit 412C by the processor 408C and retrieved as needed by the computing device 120 (FIG. 1) as used by the care provider 101. The memory unit 412C may also include storage capacity for configuration information 422 associated with the sensor devices 142(N) assigned to the patient 103 by the care plan as defined by the care provider 101 using the computing device 120. The memory unit 412C may also include control setup instructions 426. The control setup instructions 426 enables the software applications 414C of the remote server 110 to establish connectivity with the control device 135 via the I/O devices 410C of the remote server 110. The control setup instructions 426 may include the identifier information (e.g., MAC address) and the password of the control device 135 assigned to the patient 103. The memory unit 412C may also include storage capacity for the patient-specific information 424 received from the computing device 120. The patient-specific information 424 may be transferred to the control device 135 once connectivity is established between the control device 135 and the remote server 110. In this manner, the memory unit 412C contains data and instructions needed for establishing connectivity with the control device 135 so that the control device may manage the sensor device 142(N) according to the care plan.

Figure 3:
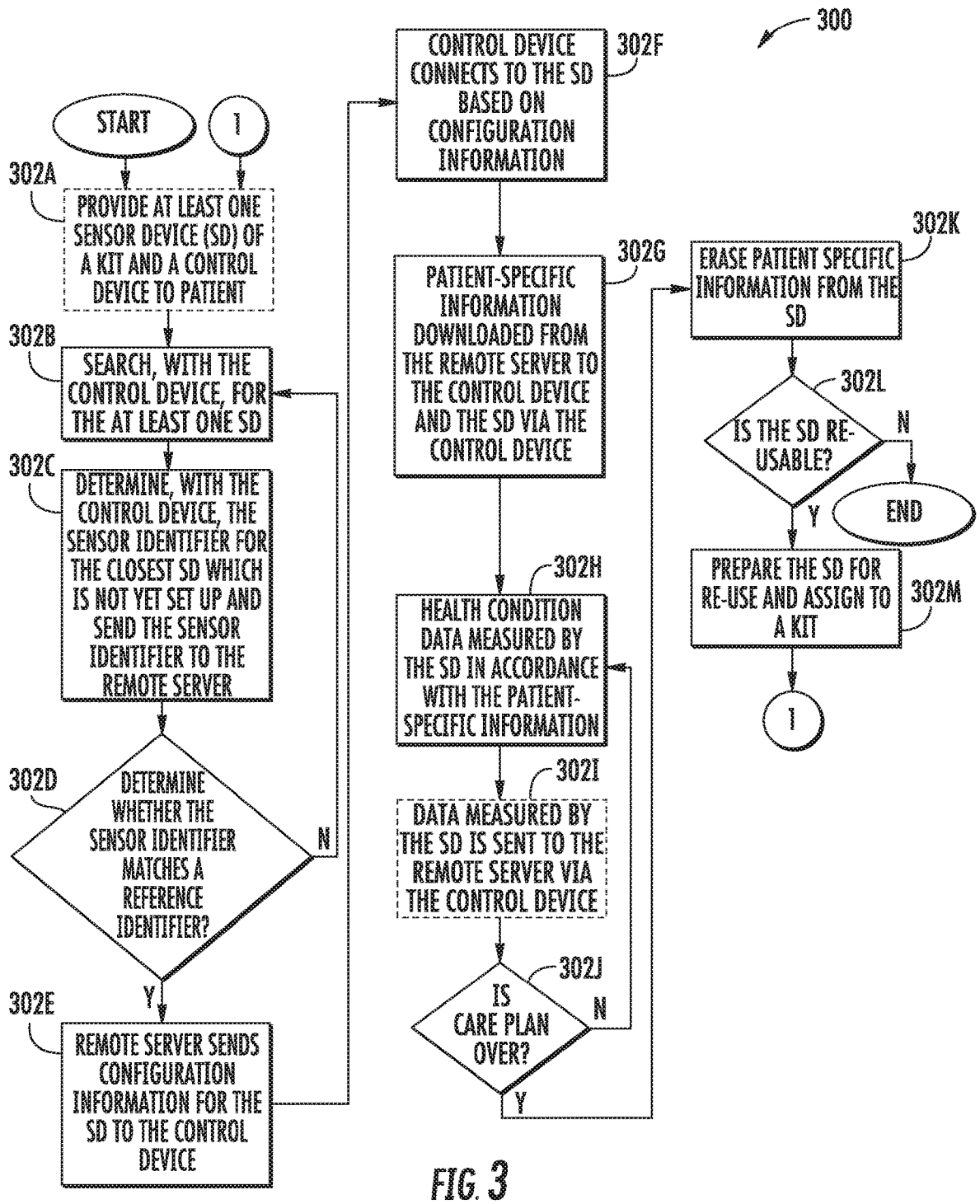
FIG. 3 is flowchart of an exemplary method of determining health condition data for a patient according to a care plan, according to one embodiment described herein.

Now that the sensor device 142(N), the control device 135, and the remote server 110 have been discussed in the context of the patient environment 130 and the care provider environment 105, FIG. 3 is a flowchart of an exemplary method 300 of determining health condition data for the patient 103 according to a care plan. The method 300 is discussed using the terminology discussed above with reference to operations 302(A)-302(M) of FIG. 3.

Figure 4A:
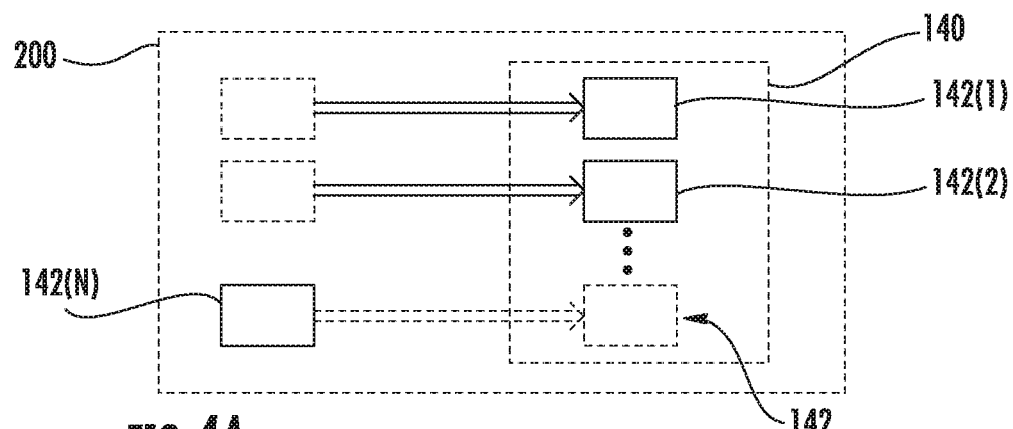
FIG. 4A is a partial schematic drawing of the care provider environment of FIG. 1, wherein the at least one sensor device are assigned to a kit, according to one embodiment described herein, according to one embodiment described herein.

In this regard, the method 300 includes providing the at least one sensor device 142(N) of the kit 140 and the control device 135 to the patient 103 (operation 302A of FIG. 3). Providing these devices to the patient 103 involves determining which of the sensor devices 142 are assigned to the patient as part of the care plan. This determining may occur in the care provider environment 105. The sensor devices to be sent to the patient 103 as part of the care plan may be provided as part of a kit 140. FIG. 4A is a partial schematic drawing of the care provider environment 105 of FIG. 1, wherein the at least one sensor devices 142 are assigned to the kit 140. In this example, the body sensor 142(1), and a blood pressure cuff 142(2) have been added to the kit 140, and the weighing scale 142(N) may also be added. Which of the at least one sensor devices 142(1)-142(N) to be added to the kit 140 may be based upon standard or typical combinations of the at least one sensor devices 142 offered. For example, patient 103 under a care plan for a heart attack of a particular severity may be prescribed a body sensor 142(1) and a blood pressure monitor 142(2). However to continue this non-limiting example, an overweight diabetic with heart pain may be prescribed use of the body sensor 142(1), the blood pressure cuff 142(2), and the weighing scale 142(N). Depending on various factors including sensor device cost, shipping charges, and convenience, more devices of the at least one sensor devices 142(1)-142(N) may be provided to the patient 103 than is specified by the care plan assigned to the patient 103 for immediate use by the patient 103. Various ones of the sensor devices 142(1)-142(N) may be enabled and disabled to facilitate a patient use schedule as provided by the care plan. In this manner, various ones of the at least one sensor device 142(1)-142(N) may be included as part of the kit 140 to be sent to the patient 103.

Figure 4B:
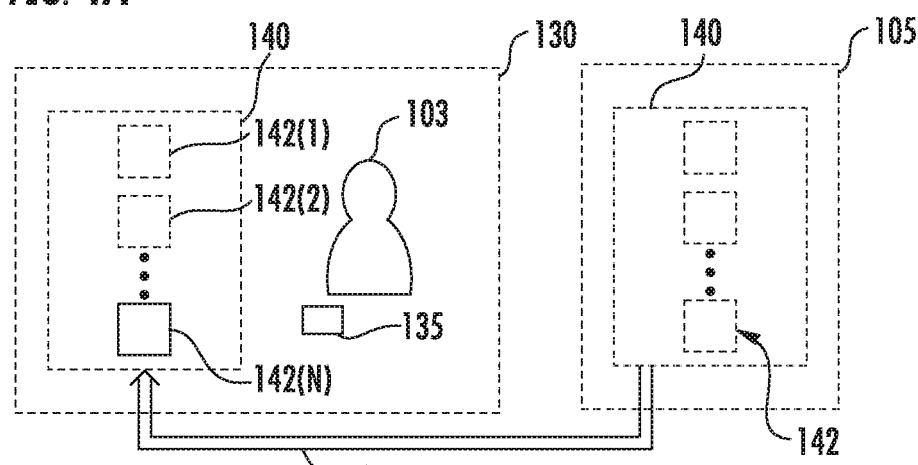
FIG. 4B is a partial schematic drawing of the care provider environment and the patient environment of FIG. 1, wherein the kit of FIG. 4A is transferred from the care provider environment to the patient environment, according to one embodiment described herein.

The kit 140 is sent to the patient 103 by physical transfer from the provider environment 105 to the patient environment 130. FIG. 4B is a partial schematic drawing of the care provider environment 105 and the patient environment 130 of FIG. 1, wherein the kit 140 of FIG. 2A is transferred from the care provider environment 105 to the patient environment 130, according to one embodiment described herein. The kit 140 may include the control device 135. In one case, the monitoring application 136 may be a software article of the kit 140 which is downloaded to the control device 135 which may already be in the possession of the patient 103 in the form of a smart phone or other personal computing device. When the kit 140 is transferred in a physical movement 204 to the patient 103, then at least one of the sensor devices 142(1)-142(N) may be disposed proximate to the control device 135. In this exemplary manner, the at least one sensor device 142(N) may be made available for subsequent connection to the control device 135.

Figure 4C:
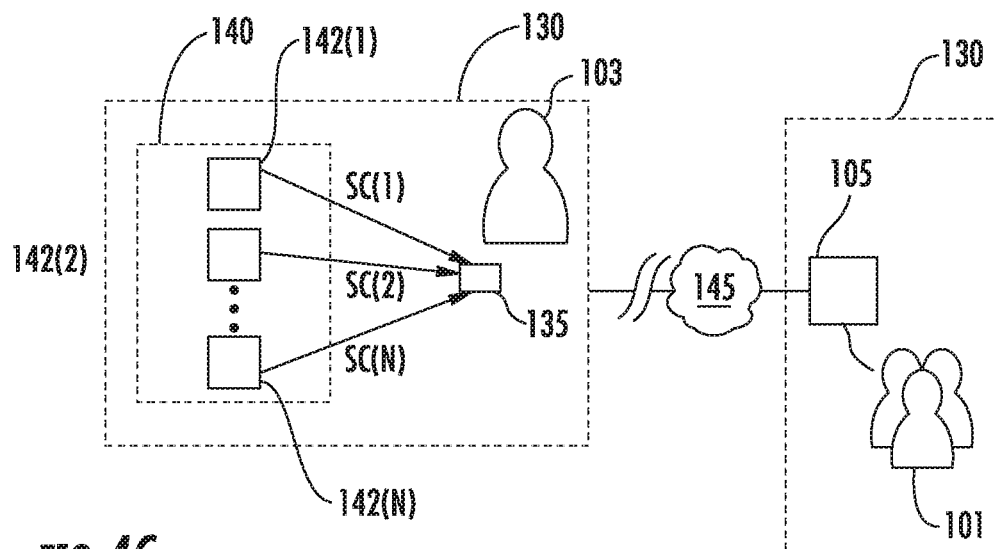
FIG. 4C is a schematic drawing of the computing environment of FIG. 1, wherein the at least one sensor device of the kit of FIG. 4B broadcasts connection signals received by a control device, according to one embodiment described herein.

The method 300 further includes searching, with the control device 135, for the at least one sensor device 142(N) (operation 302B of FIG. 3). In one case the searching may include identifying all sensor devices 142(1)-142(N) that are broadcasting a connection signal SC(1)-SC(N) as depicted in the schematic drawing of FIG. 4C. FIG. 4C is a schematic drawing of the computing environment 100 of FIG. 1, wherein the at least one sensor device 142(N) of the kit 140 of FIG. 2B broadcasts connection signals received by the control device 135. The control device 135 receives these connection signals SC(1)-SC(N) and determines the respective sensor identifiers (e.g., MAC addresses) for these sensor devices 142(1)-142(N). In this manner, the sensor devices 142(1)-142(N) broadcasting the connection signals are identified for possible connection to the control device 135.

The method 300 further includes determining, with the control device, the sensor identifier for the closest one of the sensor devices 142(1)-142(N) which is not yet set up and sends the sensor identifier to the remote server 110 (operation 302C of FIG. 3). The control device 135 may use the strength of the signal (e.g., received signal strength indication or RSSI) to determine the closest device yet unconnected to the control device 135 and send the respective sensor identifier to the remote server 110, so that it can be determined whether the care plan for the patient 103 specifies use of the sensor device, for purposes of discussion the sensor device 142(N).

The sensor device 142(N) can then be authenticated and, upon successful authentication of the sensor device 142(N), the control device 135 can configure the sensor device 142(N) in accordance with a patient care plan. In this regard, the method 300 further includes determining whether the sensor identifier of the sensor device 142(N) matches a reference identifier (operation 302D of FIG. 3). The reference identifier associated with the sensor device 142(N) is assigned by the care provider in the care plan for the patient 103. Likewise, the sensor identifier of the sensor device 142(N) is embedded within a memory of the sensor device 142(N) by the device's manufacturer. If no match is determined for that sensor identifier, then the control device 135 returns to operation 302B (FIG. 3) to continue searching. Alternatively, if a match is determined, then the remote server 110 sends configuration information (e.g., password) for the sensor device 142(N) associated with the sensor identifier to the control device 135 (operation 302E of FIG. 3). With the configuration information from the remote server 110, the control device connects to the sensor device 142(N) based on configuration information (operation 302F of FIG. 3). In this manner, the control device 135 and the sensor device may exchange information.

In one embodiment, the patient can select (e.g., using an interface of the control device 135) one or more types of authentication to be used in authenticating the sensor device 142(N). For instance, in addition to or in lieu of authenticating the sensor device 142(N) based on the device's sensor identifier, the patient may select to provide a reference identifier to the control device 135 (e.g., using an input/output device of the control device 135). For instance, such a reference identifier could be a piece of information that should be known only by the patient. Examples of the reference identifier include, without limitation, the patient's date of birth, a passcode set by the patient, and so on. The control device 135 could then transmit the reference identifier (e.g., in an encrypted form) to the remote server 110 and, upon validating the reference identifier (e.g., by comparing the received reference identifier to a preconfigured reference identifier stored on the remote server 110), the remote server 110 could confirm the authentication of the sensor device 142(N). Of course, in the event the received reference identifier does not match the preconfigured reference identifier, the remote server 110 could reject the authentication of the sensor device 142(N).

Once the connection is established, patient-specific information may be downloaded from the remote server 110 to the control device 132 and the sensor device 142(N) via the control device 135 (operation 302G of FIG. 3). The patient-specific information enables the sensor device 142(N) to set performance thresholds or other limits as the sensor device 142(N) is used by the patient 103 as part of the care plan. In this manner, the sensor device in combination with the control device 135 is prepared to be used by the patient 103 as part of the care plan.

Figure 5A:
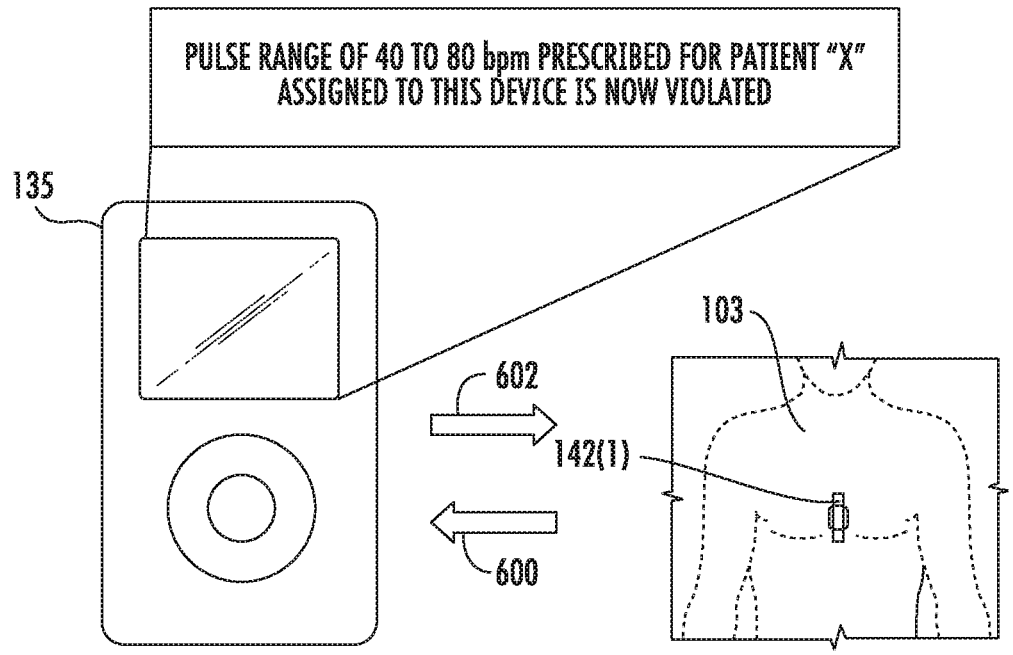
FIGS. 5A through 5D are schematic drawings of the at least one sensor device of FIG. 2 connected to the control device, wherein the at least one sensor device respectively includes: an electrocardiogram (ECG) or pulse measuring device, a blood pressure monitor, an exercise device, and a weight scale, according to embodiments described herein.

The method 300 further includes measuring health condition data 600 (FIG. 5A) of the patient, with the sensor device, in accordance with the patient-specific information (operation 302H of FIG. 3). In one illustrative example of patient-specific information utilization depicted in FIG. 5A, the sensor device may include the body sensor 142(1) which collects health condition data 600 in the form of electrocardiogram and other heart information. The patient-specific information 602 may include information related to the threshold performance of the heart of the patient as provided by the care provider. In this case, at least one of the control device 135 and the sensor device 142(1) may compare the patient-specific information 602 to the health condition data 600 to determine health events that may be communicated to the patient and/or the care provider. In the case depicted in FIG. 5A the patient-specific information includes a target pulse rate range between 40 and 80 beats per minutes, and the body sensor 142(1) measures health condition data 600 outside of this range, so the control device provides a message to the patient of "pulse range of 40 to 80 bpm prescribed for Patient 'X' assigned to this device is now violated." It is contemplated that a message could also be provided to the patient 103 at the body sensor 142(1).

In a particular embodiment, the control device 135 may receive the health condition data 600 from the sensor device 142(1), and send the health condition data 600 to a remote server (e.g., remote server 110 within care provider environment 105) for processing. The remote server, in turn, could evaluate the health condition data 600 against the patient-specific information 602 and could respond to the control device 135 with a message to be displayed by the control device 135, according to the care plan performance thresholds set on the remote server. Doing so maintains the care plan performance thresholds in a centralized location on the remote server.

Figure 5B:
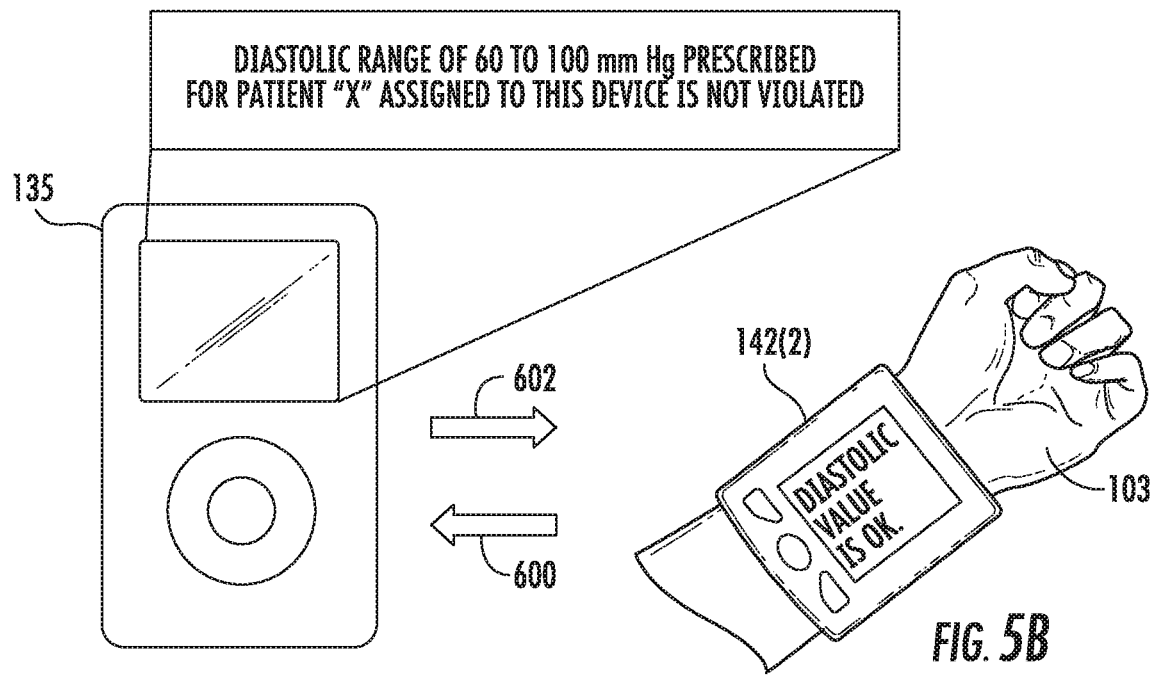

In another example, depicted in FIG. 5B, the sensor device may include a blood pressure monitor 142(2) measuring health condition data 600 including blood pressure. The patient-specific information 602 includes a target diastolic range of 60 to 100 mm Hg. The control device 135 may compare the health condition data 600 to the patient-specific information 602 and generate the message "Diastolic range of 60 to 100 mm Hg prescribed for patient 'X' assigned to this device is not violated" to be displayed. The blood pressure monitor 142(2) may also compare the health condition data 600 to the patient-specific information 602 and display the message "Diastolic value is OK" for the patient.

Figure 5C:
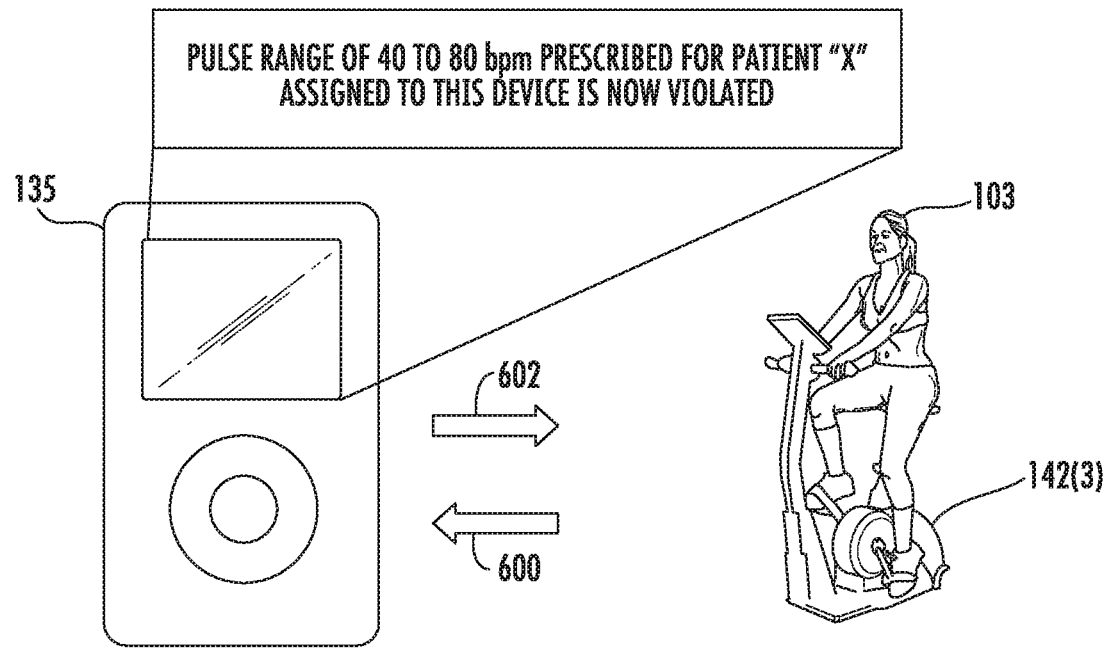

In another example, depicted in FIG. 5C, the sensor device may include an exercise device 142(3) measuring health condition data 600 including a pulse of the patient 103. The patient-specific information 602 includes a target pulse range of 40 to 80 beats per minute (bpm). The control device 135 may compare the health condition data 600 to the patient-specific information 602 so that when necessary the message "Pulse range of 40 to 80 bpm prescribed for patient 'X' assigned to this device is now violated" may be displayed.

Figure 5D:
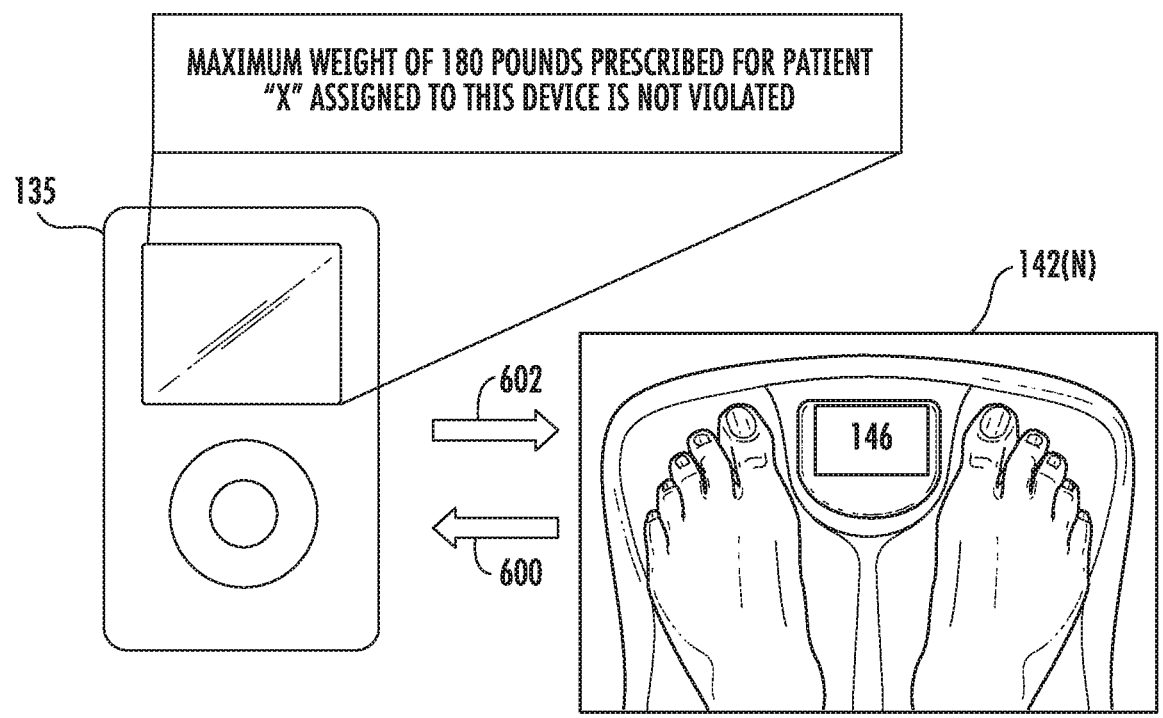

In another example, depicted in FIG. 5D, the sensor device may include a weight scale 142(N) measuring health condition data 600 including a weight of the patient 103. The patient-specific information 602 may include a weight range of less than 150 pounds according to the care plan defined by the care provider. The control device 135 may use the health condition data 600 to compare to the patient-specific information 602 so that when necessary the message "maximum weight of 150 pounds prescribed for patient 'X' assigned to this device is not violated" may be displayed. In these examples, the health condition data may be compared to the patient-specific information.

The method 300 may further include sending health condition data measured by the sensor device 142(N), to the remote server 110 via the control device 135 (operation 302I of FIG. 3). In other examples, the health condition data may remain at the sensor device 142(N) without being sent to the remote server 110 if notification of only the patient is specified by the care plan.

The method 300 further includes determining whether the care plan is over (operation 302J of FIG. 3). If it is determined that the care plan is not over, then the sensor device 142 continues to measure health condition data according to operation 302H. Alternatively, if the care plan is over, then the patient-specific information is erased from the sensor device 142(N) (operation 302K of FIG. 3). In some cases the patient specific information may also be erased from the control device 135. In this manner, the patient-specific information may be protected.

The method 300 further includes determining whether the sensor device 142(N) is re-usable (operation 302L of FIG. 3). The determination may be based on whether the sensor device 142(N) is disposable or has been damaged during use. If the sensor device 142(N) is determined not to be re-usable, then the sensor device 142(N) may be discarded as the method 300 ends. Alternatively, the sensor device 142(N) may be returned to the care-provider environment, prepared for re-use, and may be assigned to a kit 140 for distribution to a different patient 103 (operation 302M of FIG. 3). Once preparation for re-use is completed, then operation 302A may begin again. In this manner, the health condition data may be measured from a patient 103.

Figure 6:
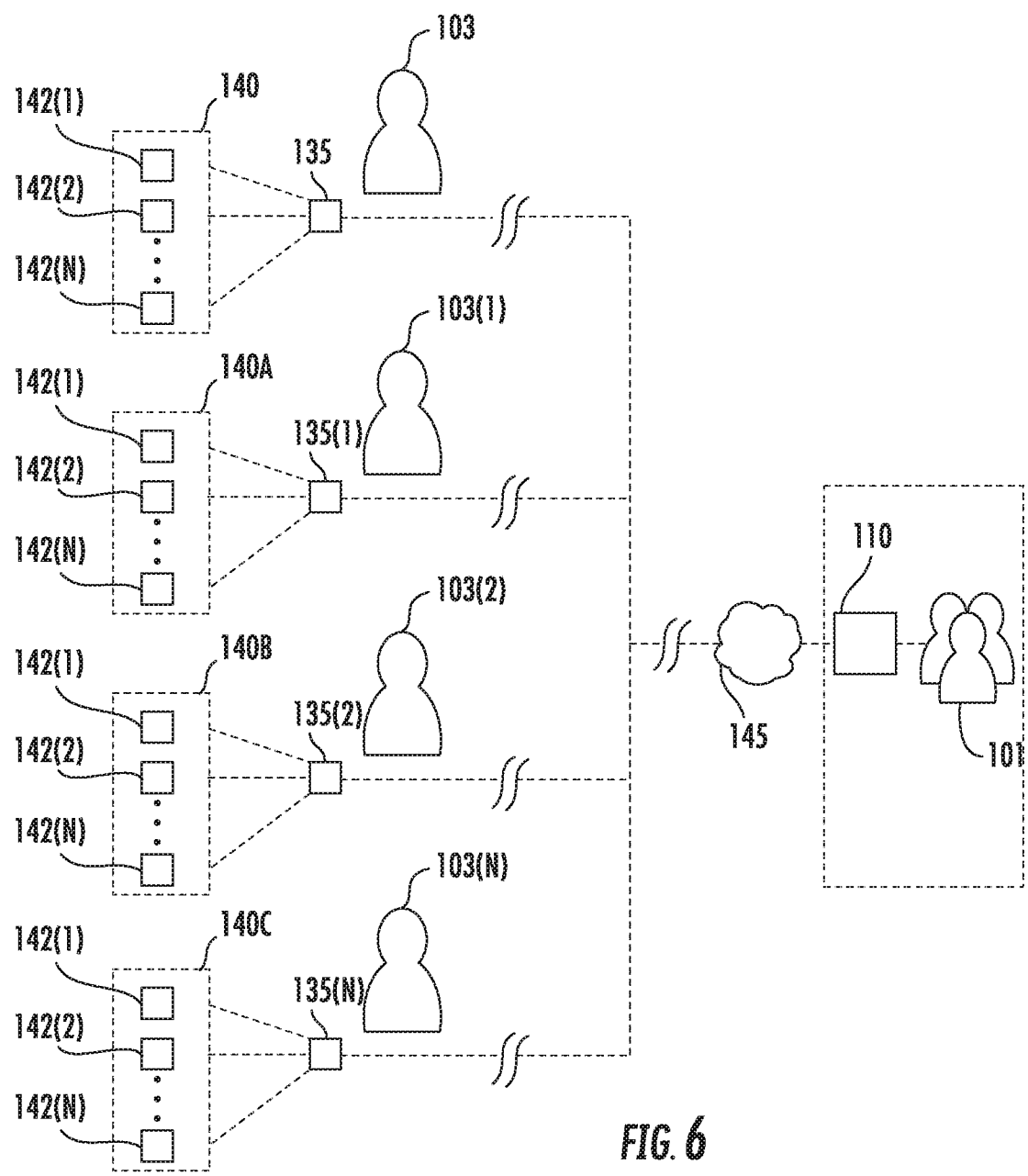
FIG. 6 is a schematic drawing of an exemplary computing environment of FIG. 1, wherein a plurality of control devices may configure respective sensor devices of a plurality of kits, according to one embodiment described herein.

Now that the method 300 has been introduced, it is recognized that several kits 140-140C of sensor devices may be connected to control devices 135-135(N) and the remote server 110 as depicted in FIG. 6. While FIG. 6 depicts kits 140-140C connected to control devices 135-135(N), more generally any number of kits can be connected to the remote server 110 via control devices, according to embodiments described herein.

In the preceding, reference is made to embodiments presented in this disclosure. However, the scope of the present disclosure is not limited to specific described embodiments. Instead, any combination of the described features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the preceding aspects, features, embodiments and advantages are merely illustrative and are not considered elements or limitations of the appended claims except where explicitly recited in a claim(s).

As will be appreciated by one skilled in the art, the embodiments disclosed herein may be embodied as a system, method or computer program product. Accordingly, aspects may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium is any tangible medium that can contain, or store a program for use by or in connection with an instruction execution system, apparatus or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described below with reference to flowchart illustrations and/or block diagrams of methods, apparatus (systems) and computer program products according to embodiments presented in this disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality and operation of possible implementations of systems, methods and computer program products according to various embodiments. In this regard, each block in the flowchart or block diagrams may represent a module, segment or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In view of the foregoing, the scope of the present disclosure is determined by the claims that follow.

What is claimed is:

1. A method, comprising:
   searching for one or more care plan devices, using a control device, based on one or more wireless transmissions between the one or more care plan devices and the control device, and in response detecting a first care plan device of the one or more care plan devices;
   receiving, at the control device from the first care plan device using a wireless message, a device identifier, wherein the device identifier is written to a memory of the first care plan device by a manufacturer;
   transmitting the device identifier from the control device to a remote server;
   receiving at the control device an indication from the remote server that the first care plan device is specified for use by a patient in a patient care plan;
   receiving, at the control device from the remote server, configuration information for the first care plan device according to the patient care plan; and
   configuring the first care plan device using the control device, according to the patient care plan, based on the received configuration information.

2. The method of claim 1, wherein configuring the care plan device further comprises establishing a connection between the control device and the care plan device, initiated upon the control device receiving the configuration information for the care plan device.

3. The method of claim 1, wherein the configuration information for the care plan device comprises patient care plan information.

4. The method of claim 1, wherein the care plan device is a sensor device, and wherein configuring the care plan device to monitor data values for at least one type of biometric data further comprises configuring the care plan device to detect when one of the data values for the at least one type of biometric data exceeds a predefined threshold.

5. The method of claim 1, wherein configuring the care plan device in accordance with the patient care plan further comprises configuring the care plan device with a set of assigned patient tasks specified in the patient care plan.

6. The method of claim 1, further comprising:
   collecting patient-specific biometric data using the care plan device; and
   determining that the care plan is over, and in response erasing the patient-specific biometric data from the care plan device and the control device.

7. The method of claim 1, wherein the control device comprises a personal computing device, wherein the care plan device comprises a biometric sensor device, and wherein the care plan device communicates with the remote server using the control device.

8. The method of claim 1, further comprising:
   detecting a second care plan device using the control device; and
   receiving, at the control device from the remote server, an indication that the second care plan device is not specified for use by the patient in the patient care plan, and in response disabling the second care plan device using the control device.

9. The method of claim 8, wherein disabling the second care plan device using the control device comprises transmitting a disable code from the control device to the second care plan device.

10. The method of claim 1, further comprising:
    authenticating the first care plan device based on transmitting an encrypted reference identifier relating to the patient from the control device to the remote server.

11. The method of claim 10, wherein the encrypted reference identifier comprises a passcode set by the patient.

12. The method of claim 1, wherein the configuration information for the first care plan device received from the remote server further comprises a password for the first care plan device, the method further comprising:
    establishing a connection between the control device and the first care plan device using the password received from the remote server.

13. The method of claim 1, wherein the searching for one or more care plan devices is based on a strength of a wireless signal between the control device and at least one of the one or more care plan devices.

14. A control device, comprising:
a processor; and
a memory containing computer program code that, when executed, performs an operation comprising:
   searching for one or more care plan devices, using the control device, based on one or more wireless transmissions between the one or more care plan devices and the control device, and in response detecting a first care plan device of the one or more care plan devices;
   receiving, at the control device from the first care plan device using a wireless message, a device identifier, wherein the device identifier is written to a memory of the first care plan device by a manufacturer;
   transmitting the device identifier from the control device to a remote server;
   receiving at the control device an indication from the remote server that the first care plan device is specified for use by a patient in a patient care plan;
   receiving, at the control device from the remote server, configuration information for the first care plan device according to the patient care plan; and
   configuring the first care plan device using the control device, according to the patient care plan, based on the received configuration information.

15. The control device of claim 14, wherein configuring the care plan device further comprises establishing a connection between the control device and the care plan device, initiated upon the control device receiving the configuration information for the care plan device.

16. The control device of claim 14, wherein the configuration information for the care plan device comprises patient care plan information.

17. The control device of claim 14, wherein the care plan device comprises a sensor device, and wherein configuring the care plan device to monitor data values for at least one type of biometric data further comprises at least one of:
   (i) configuring the care plan device to detect when one of the data values for the at least one type of biometric data exceeds a predefined threshold; and
   (ii) configuring the care plan device to detect transmit the data values for the at least one type of biometric data to the remote server, wherein logic on the remote server is configured to detect when the data value exceeds the predefined threshold.

18. The control device of claim 14, wherein configuring the care plan device in accordance with the patient care plan further comprises configuring the care plan device with a set of assigned patient tasks specified in the patient care plan.

19. A non-transitory computer-readable medium containing computer program code that, when executed, performs an operation comprising:
   searching for one or more care plan devices, using a control device, based on one or more wireless transmissions between the one or more care plan devices and the control device, and in response detecting a first care plan device of the one or more care plan devices;
   receiving, at the control device from the first care plan device using a wireless message, a device identifier, wherein the device identifier is written to a memory of the first care plan device by a manufacturer;
   transmitting the device identifier from the control device to a remote server;
   receiving at the control device an indication from the remote server that the first care plan device is specified for use by a patient in a patient care plan;
   receiving, at the control device from the remote server, configuration information for the first care plan device according to the patient care plan;
   configuring the first care plan device using the control device, according to the patient care plan, based on the received configuration information; and
   receiving, from the remote server, updated configuration information for the first care plan device according to an updated patient care plan, wherein the remote server is configured to transmit the updated configuration information responsive to detecting a change in the patient care plan.

20. The non-transitory computer-readable medium of claim 19, wherein configuring the care plan device in accordance with the patient care plan further comprises configuring the care plan device with a set of assigned patient tasks specified in the patient care plan.

* * * * *